(12) United States Patent
Garvin (10) Patent No.: US 6,329,180 B1
(45) Date of Patent: Dec. 11, 2001

(54) GENETIC ANALYSIS USING PEPTIDE TAGGED IN-VITRO SYNTHESIZED PROTEINS

(76) Inventor: Alex M. Garvin, 1 rue des Bois, Durmenach (FR), 68480

( * ) Notice: Subject to any disclaimer, the term of this patent is extended or adjusted under 35 U.S.C. 154(b) by 0 days.

(21) Appl. No.: 09/266,462

(22) Filed: Mar. 11, 1999

Related U.S. Application Data (63) Continuation-in-part of application No. PCT/US96/14708, filed on Sep. 13, 1996.
(51) Int. Cl.[7] .............................. C12Q 1/68; C12P 19/34; C07K 5/00; C07K 17/00; A23J 1/00
(52) U.S. Cl. ..................... 435/91.2; 435/6; 435/91.2; 435/69.1; 530/300; 530/350; 530/412; 530/413
(58) Field of Search ........................ 435/91.2, 6, 69.1; 530/300, 350, 412, 413

(56) References Cited

U.S. PATENT DOCUMENTS

| | | | |
|---|---|---|---|
| 5,800,998 | * | 9/1998 | Glucksmann .............................. 435/6 |
| 5,925,748 | * | 7/1999 | Stone et al. ........................... 536/23.1 |
| 6,207,370 | | 3/2001 | Little et al. ............................... 435/6 |

FOREIGN PATENT DOCUMENTS

| | | | |
|---|---|---|---|
| 99/12040 | 3/1999 | (WO) | .............................. G01N/33/68 |

OTHER PUBLICATIONS

Dongen et al., Rapid analysis of enzymatic digests of a bacterial protease of the subtilisin type and a "bio–engineered" variant bny high–performance liquid chromatography–frit fast atom bombardment mass spectrometry. J. of Chromatography, vol. 647, pp. 301–309, 1993.*
Sarfati et al. Evidence of a new serine protease in the rat pure pancreatic juice that degrades somatostatin, Life Science, vol. 47, pp. 1043–1049, 1990.*
Schuerch et al. Enhanced mass resolution in matrix–assisted laser desorption/ionization linear time–of–flight mass spectrometry (the abstract). vol. 23(11), pp. 695–700, 1994.*
Powell, et al., "Molecular Diagnosis of Familial Adenomatous Polyposis," *New England Journal of Medicine*, 329, 1982–1987 (Dec. 30, 1993).
Hogervorst et al., "Rapid detection of BRCA1 mutations by the protein truncation test," *Nature Genetics*, 10, 208–212 (Jun. 1995).
Bodmer et al., Imperial Cancer Research Fund Scientific Report 1995.
Garvin, Alex M., "A Complete protein truncation test for BRCA1 and BRCA2," *European Journal of Human Genetics*, 6, 226–234 (1998).

* cited by examiner

Primary Examiner—Stephanie W. Zitomer
Assistant Examiner—Joyce Tung
(74) Attorney, Agent, or Firm—Testa, Hurwitz & Thibeault, LLP (57) ABSTRACT

A method and kit are disclosed useful for detecting protein altering mutations in genes. The coding sequence of the gene is PCR amplified with a 5' primer that contains at its 5' end a polymerase binding site, a translation initiation site, and an in frame sequence coding for a peptide tag, followed by the in frame 5' end of the test sequence. The coding sequence for the peptide tag can also be incorporated into the 3' primer used for PCR. After PCR amplification of the test sequence, the PCR product is used as a template to make mRNA in an in-vitro transcription reaction using an RNA polymerase that recognizes the polymerase binding site incorporated into the 5' PCR primer. The mRNA is then used as a template to make protein in an in-vitro translation reaction. The protein encoded by the test sequence has at its amino or carboxy terminus a peptide tag that can be used to purify the protein for further analysis. For example, the mass of the purified protein can be determined by mass spectrometry in order to detect protein-altering mutations. Examples are disclosed using matrix assisted laser desorption ionization (MALDI) time-of-flight (TOF) mass spectrometry instruments to analyze proteins of interest.

10 Claims, 8 Drawing Sheets

GENETIC ANALYSIS USING PEPTIDE TAGGED IN-VITRO SYNTHESIZED PROTEINS

CROSS REFERENCE TO RELATED APPLICATION

This patent application is a continuation-in-part of copending International Application Serial No. PCT/US96/14708, filed on Sep. 13, 1996, which is incorporated by reference in its entirety.

FIELD OF INVENTION

This invention relates to methods and kits for detecting mutations in genes by synthesizing in-vitro the proteins encoded by the genes with a peptide tag attached to the amino or carboxy termini, and analyzing the properties of the tagged proteins. In particular, this invention relates to the use of mass spectrometry for analyzing the tagged, and optionally purified proteins.

BACKGROUND OF THE INVENTION

Many genes that predispose to human disease have now been identified and hundreds more will be found over the next decade. In order to take advantage of these findings, the biomedical community must be able to identify individuals that carry mutations in these genes in order to counsel them and to help them take preventative measures.

The methods now being used to screen for mutations in certain disease causing genes suffer from short comings that will make it far too time consuming and expensive to carry out large scale screenings. For example, the breast cancer susceptibility genes BRCA1 and BRCA2 recently have been identified, and mutations predisposing a human to breast cancer have been found throughout the 16 kilobases of coding sequence contained in these two genes. The entire coding sequences of BRCA1 and BRCA2 are now routinely screened by DNA sequencing, Single Strand Conformation Polymorphism (SSCP), or the Protein Truncation Test (PTT). All three of these techniques rely on the electrophoretic properties of either DNA or protein, and detection of the electrophoresed products is accomplished by incorporation of a labeled tag. The label may be either a fluorescent or radioactive. Sequencing both strands of the 16 kb of BRCA½ for a single individual is costly and tedious with current techniques and gives a large amount of redundant information, since virtually all of the sequence will be identical to the known sequence. SSCP is less tedious, but still requires sequencing benign polymorphisms. Furthermore, SSCP segment length is limited to 150 base pairs, requiring a minimum of 6 PCR reactions per kilobase screened. PTT is the fastest of these techniques but it is incapable of detecting missense mutations, and also suffers from all of the drawbacks of gel electrophoresis, such as gel preparation, long running times, and low resolution.

Other techniques such as Allele Specific Oligomer Hybridization and Allele Specific PCR are designed to identify one previously characterized mutation per assay. These techniques are useful when a particular mutation has already been identified and is widespread, but cannot be used for genes where a large number of yet unidentified mutations exist in the human population.

Thus, a need exists for a reliable, high throughput method for gene mutation detection which takes advantage of the speed, sensitivity, accuracy and resolving power of analytical measurement instruments such as mass spectrometry instruments.

SUMMARY OF THE INVENTION

The present invention consists of a method for identifying genetic mutations by synthesizing proteins in-vitro and characterizing the protein product. The proteins are preferably synthesized with a peptide tag attached to their amino and/or carboxy terminus. In accordance with various embodiments of the method, the template for the in-vitro RNA and protein synthesis reactions can be a double stranded DNA polymerase chain reaction (PCR) product containing a test sequence of interest, although other forms of DNA can be used as well. When PCR products are used, the peptide tag can be encoded by a sequence present in either a 5' primer or 3' primer used to PCR amplify the test sequence. Any continuous stretch of coding sequence present in either genomic DNA or cDNA may be amplified with such primers, and the PCR product will have a sequence encoding the peptide tag in frame and adjacent to the test sequence. Any tagged test protein may be purified by means of an immobilized ligand specific for the tag, regardless of the composition of the test sequence.

The peptide tag may be used adjacent to any test sequence, and the assay can be multiplexed by incorporating different peptide tags with different test sequences so that different in-vitro synthesized proteins may be purified and analyzed separately.

Many ligands have been developed or discovered which bind with high affinity and specificity to particular peptides, among the most useful being monoclonal antibodies. Ligands of this type can be coupled to a solid support, for example, packed in an affinity chromatography column, and used to immunopurify peptide tagged proteins from complex mixtures rapidly and with high efficiency. Once the tagged test protein is purified from the other components of the cell lysate required for protein synthesis, it can be analyzed by various analytical instrument techniques, such as by mass spectrometry. In accordance with one embodiment, the purified protein is analyzed by the use of matrix assisted laser desorption ionization time-of-flight (MALDI-TOF) mass spectroscopy. Any single alteration in the DNA test sequence that alters the amino acid composition, and hence the mass of the protein product which it encodes, can be detected by the method of the present invention. One exception would be multiple alterations which cancel out each other's effects. However, such multiple mutations would be extremely rare. Also, leucine and isoleucine have the same mass, and an exchange of these residues will not alter the mass of the protein product.

The present invention provides several advantages. One important advantage is the elimination of the need to conduct electrophoretic separations of protein mixtures. In this manner, the speed and throughput of this method of analysis is significantly enhanced. Also, since the method provides a direct measure of mass, and not an inferred mass based upon electrophoretic mobility, mass accuracy is dramatically improved. Artifacts due to multiple protein folding states are completely eliminated, and mutations leading to amino acid substitutions are detectable by mass spectrometry.

These and other aspects, advantages, and objects of the present invention will be apparent from the following detailed description of the invention taken in conjunction with the drawings.

DETAILED DESCRIPTION OF THE INVENTION

Methods of the invention provide an efficient, cost effective, high throughput screen to identify patients that have a genetic abnormality in a genomic region of interest. That is, a method of the invention involves detecting a protein altering mutation in a test sequence of a gene by amplifying the test sequence using one or more oligonucleotide primers, expressing the polypeptide product encoded by the test sequence, and analyzing the expressed polypeptide product to identify the presence of a variant (non wild-type) amino acid sequence.

According to the invention, a patient that is identified as having DNA which encodes an abnormal peptide product may be subsequently tested to determine the nature of the genetic lesion responsible for the abnormality. In a preferred embodiment, the nucleotide sequence is determined for the region of the patient's genomic DNA that encodes the peptide product. Alternatively, an oligonucleotide probe hybridization assay is performed to identify a mutation is this region. Other nucleotide detection/identification assays may also be used to identify the genetic source of the peptide abnormality. The patient's prognosis may be made on the basis of the genetic abnormality that is identified. In contrast, nucleotide assays are not performed for a patient that does not encode an abnormal peptide. Accordingly, methods of the invention are useful in a population screening procedure to identify patients that are candidates for subsequent, more expensive, diagnostic testing. Methods of the invention also are useful in pharmacogenetic tests and applications to identify rapidly the presence of one or more allelic variants in a patient.

Figure 1A:
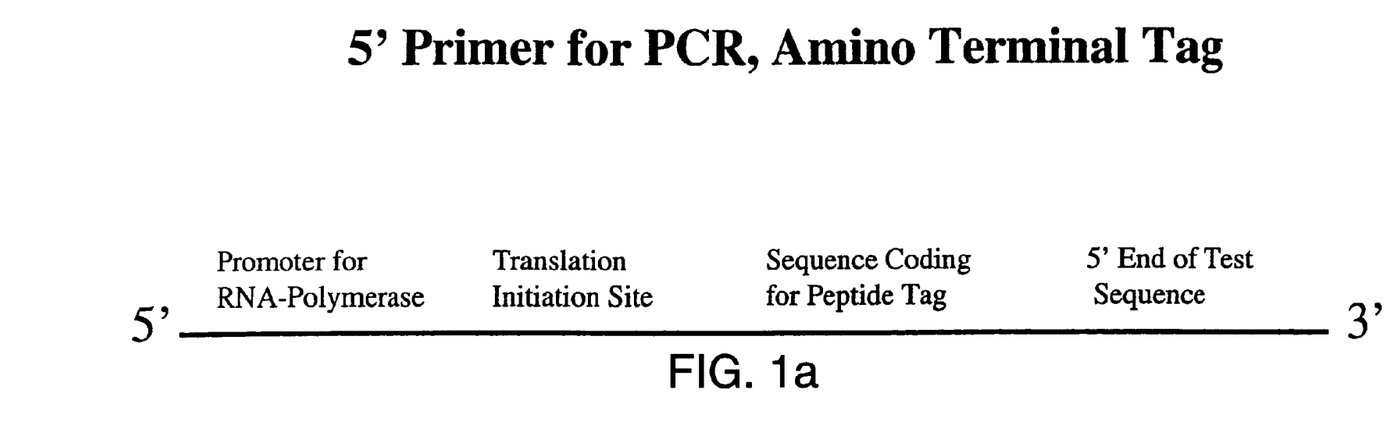
FIG. 1a shows the elements of the 5' primer used to PCR amplify a region of a test sequence where a peptide tag is attached to the amino terminus.

FIG. 1a shows a primer used in the method of the present invention. The 5' primer shown in FIG. 1a is a standard synthetic oligonucleotide (or polynucleotide) without modification at either the 5' or 3' ends. The unique features of the oligonucleotide lie in the functional properties of its sequence. From the 5' to 3' direction, at least the following four elements are present:

1) A sequence recognized by an RNA polymerase. An example is the sequence recognized by the viral T7 polymerase 5'-TAATACGACTCACTATAGGG-3' (SEQ ID No. 5).

2) A sequence that allows translation initiation of mRNA. An example is the methionine codon placed after the Kozak consensus sequence: AGACCACCATG (SEQ ID No. 6).

3) An in frame sequence coding for a peptide that can be used for detection or affinity purification (a peptide tag). An example is the sequence GAC TAC AAG GAC GAC GAT GAC AAG (SEQ ID No. 7), which codes for the FLAG peptide DYKDDDDK (SEQ ID No. 2). When the FLAG peptide is present at the amino terminus of a protein, it is recognized by the anti-FLAG M2 monoclonal antibody. The M2 antibody can be used in western blotting to detect FLAG containing proteins, or it can be used to affinity purify the protein for further analysis.

4) An in frame sequence that hybridizes to the complement of a sequence at or adjacent (preferably 5') to the 5' end of the coding sequence being tested (the coding strand of the test sequence). This 5' hybridization sequence must be of sufficient length to allow the oligomer to hybridize to the non coding strand of the test sequence present in the genomic DNA or cDNA sample and to act as a primer for PCR. Usually 20 bases are enough. An example is the in frame sequence GCT TGT GAA TTT TCT GAG AC (SEQ ID No. 8), which is complimentary to the non-coding strand at the 5' end of exon 11 of the BRCA1 gene.

Figure 1B:
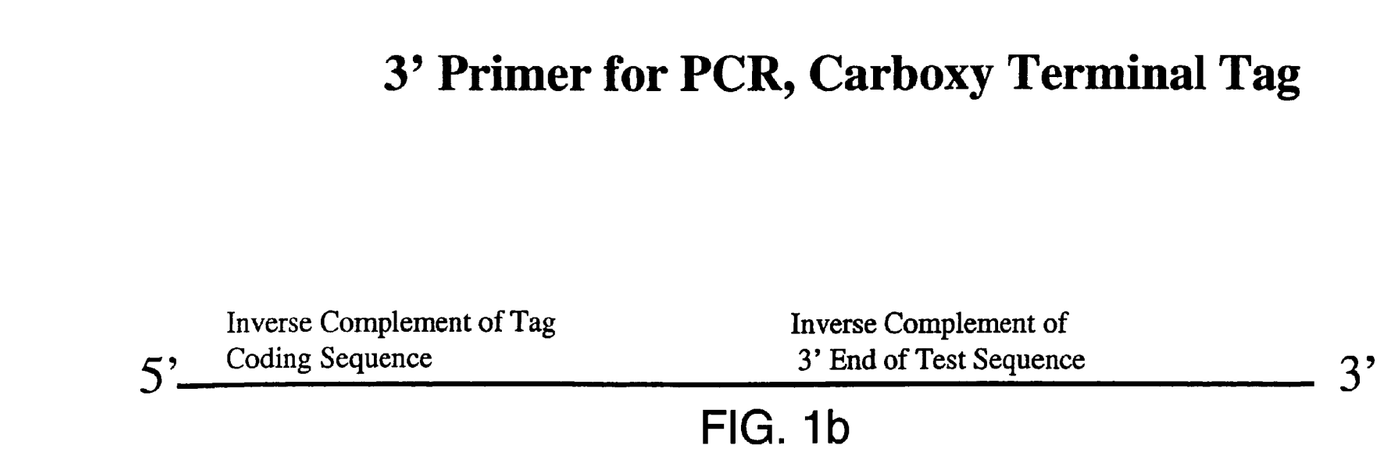
FIG. 1b shows the elements of the 3' primer used to PCR amplify a region of test sequence where a peptide tag is attached to the carboxy terminus.

FIG. 1b shows an alternative primer that may be used in the method of the present invention when the peptide tag is attached to a carboxy terminus. The 3' primer shown in FIG. 1b is a standard synthetic oligonucleotide without modification at either the 5' or 3' ends. The unique features of the oligonucleotide lie in the functional properties of its sequence. From the 5' to 3' direction, at least the following two elements are present:

1) an inverse compliment of sequence encoding the peptide tag.

2) a sequence that hybridizes to a sequence at or adjacent (preferably 3') to the 3' end of the coding strand of the test sequence.

One of ordinary skill in the art will understand that a test sequence comprises both a coding strand and a non-coding strand. The sequence information of the coding strand is reproduced in the transcribed RNA molecule, whereas the sequence information of the non-coding strand is complementary to the sequence of the transcribed RNA molecule.

Figure 2:
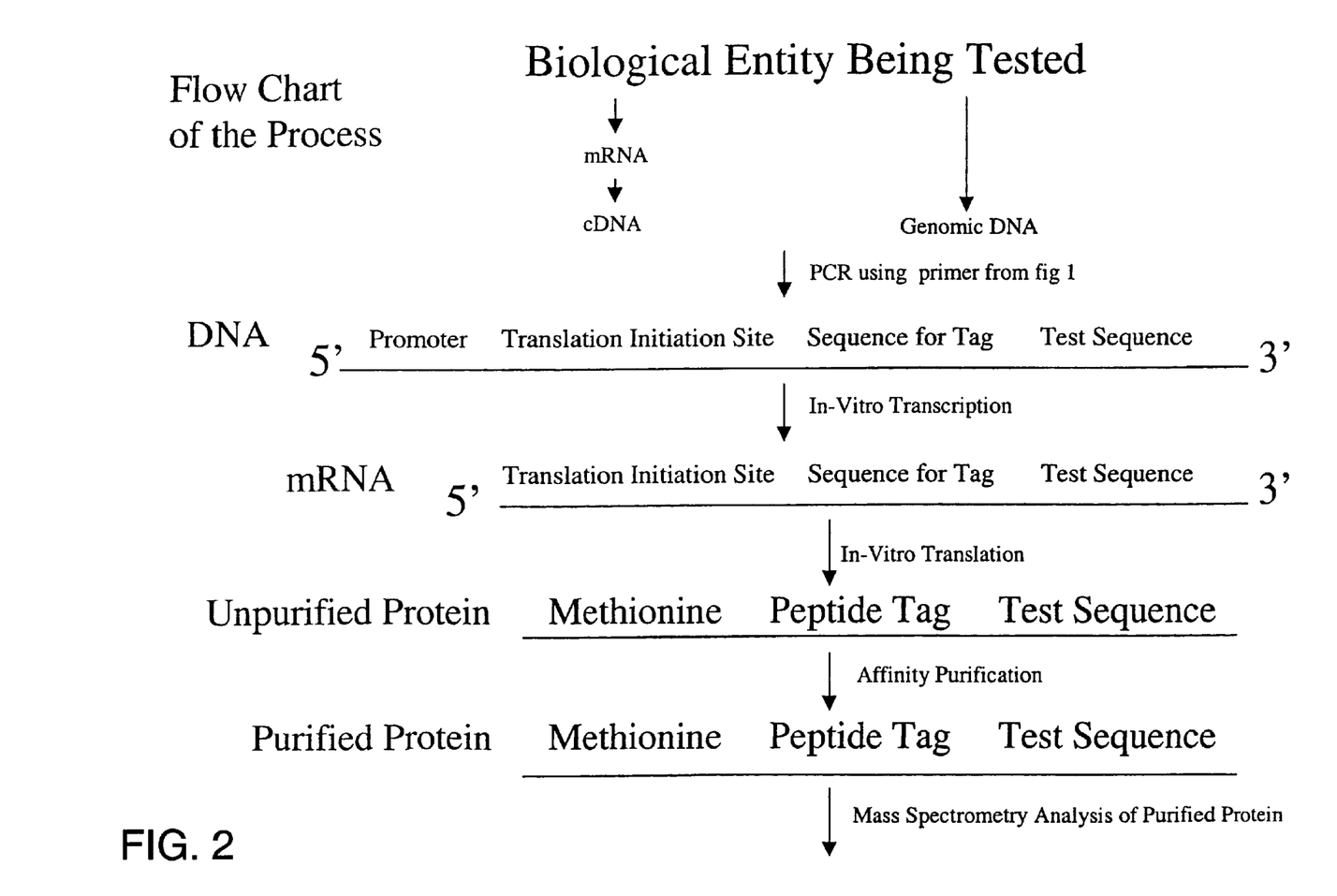
FIG. 2 shows a flow chart of a preferred method of the present invention.

The flow chart in FIG. 2 provides an overview of one embodiment of a method of the present invention.

Step 1) Preparation of Template for PCR.

The PCR reaction must amplify a continuous stretch of coding sequence. The maximum length of coding sequence that can be analyzed per segment is at least 2 kilobases, thus for genes having many small exons it will be convenient to use cDNA as template. When using cDNA as starting material for PCR, the tissue used to extract RNA must express the gene being tested. Many human genes (if not most) are expressed to some extent in peripheral blood, and can be PCR amplified from cDNA derived from peripheral blood leukocytes. Genomic DNA can be conveniently used as template for the coding sequence of large exons. It can also be used when cDNA is not available, and when mutant message is thought to be unstable. It should be noted that splice site mutations within introns and a subset of those within exons will be not be detected when genomic DNA is used as template.

Step 2) PCR.

A continuous region of in frame coding sequence for the gene of interest is amplified by the polymerase chain reaction using the 5' primer described in FIG. 1a, and a 3' primer that need not be in-frame. When cDNA is used as template and the gene is expressed at low levels in the source tissue used to make RNA, nested PCR is often required to get good amplification. An aliquot of the PCR product is used for the next step.

Step 3) In-vitro Transcription.

RNA is generated by using the PCR product from Step 2) as template in a reaction mixture containing all of the other components required for RNA synthesis. The RNA polymerase used in this step must recognize the promoter sequence at the 5' end of the PCR product.

Step 4) In- Vitro Translation.

The RNA made in Step 3) is then used as template in a cell lysate containing all the reagents required for protein synthesis. Rabbit reticulocytes and wheat germ are common lysate sources. Steps 3 and 4 could be done simultaneously using a coupled transcription/translation system, but this is not essential. In a preferred embodiment, protease inhibitors are added to the translation reaction to minimize or inhibit degradation of the synthesized polypeptide. Accordingly, a protease inhibitor increases the sensitivity of methods of the invention by increasing the amount of polypeptide product, and by reducing the background signal associated with partially degraded polypeptide products. A preferred inhibitor is Phenylmethylsulfonylflouride (PMSF), which has been shown to inhibit C-terminal degradation of a test peptide in a rabbit reticulocyte lysate when present at a concentration of 1 mM.

Step 5) Affinity Purification.

The protein made in Step 4) is present in a lysate containing thousands of different proteins, ribosomal RNA, salts, metabolites, lipids, and other components. In order to analyze this protein using some of the more sensitive techniques available (such as mass spectrometry), it is preferable to purify the protein. The peptide tag engineered into the amino-terminus (or carboxy terminus) of the protein can be used for this purpose. One way to accomplish the purification is to use a ligand specific for the peptide tag immobilized to a solid surface. For example, if the FLAG peptide is used as the peptide tag, an anti-FLAG antibody could be covalently attached to beads. After incubation of the lysate with the anti-FLAG beads to allow binding, the beads could be washed, and the test protein could be eluted from the beads. This could be accomplished with the use of an affinity chromatography system. The anti-FLAG antibody could also be immobilized on planar surfaces, magnetic beads, tubing, microplates, and the like.

Step 6) Analysis of the Polypeptide Product.

In a preferred embodiment, the synthesized polypeptide or protein product is purified. The purified product can be analyzed by a variety of techniques that measure the properties of a protein. These properties are compared to the properties of a polypeptide or protein encoded by the wild type sequence and any differences between the test protein and the control indicate that a mutation may be present. The assay used at this stage must be sensitive enough to detect the amount of material purified from the lysate. For example, 50 microliters of a rabbit reticulocyte lysate can typically provide 5 picomoles of a 50 kD protein. Mass spectroscopy can measure the mass of a protein to within 0.01% mass accuracy when low picomole amounts of the protein are available. This level of accuracy should allow for detection of mutant proteins having amino acid substitutions as well as truncations. A particularly useful mass spectrometry instrument for carrying out the protein analysis is a MALDI-TOF instrument available from PerSeptive Biosystems, Inc. under the brand name Voyager™ PRO.

In one embodiment of the invention, the test sequence is amplified using a 5' primer that encodes a peptide tag and a 3' primer that encodes a peptide tag. In a preferred embodiment, the 5' primer encoded peptide tag is different from the 3' primer encoded peptide tag. For example, the 5' peptide tag may be a MYC epitope tag and the 3' peptide tag may be a 6 HIS tag. The resulting in-vitro synthesized polypeptide has a MYC epitope tag at its N-terminal end and a 6 HIS tag at its C-terminal end. This polypeptide may be affinity purified using ligands for either one or both of these peptide tags.

In a more preferred embodiment, the in-vitro synthesized polypeptide is purified in two steps. In the first step, the polypeptide is affinity purified using a specific ligand for the first peptide tag. The product from this first purification step is further purified in a second step using a specific ligand for the second peptide tag. A ligand for either one of the N-terminal and C-terminal peptide tags may be used in the first purification step, and a ligand for the other peptide tag is used in the second purification step. The product purified in this two step procedure will be a polypeptide that results from transcription/translation of the entire amplified DNA template. This two step purification product does not include peptides that result from internal translation initiation, because such peptides do not contain the N-terminal tag, as discussed above. Similarly, the two step purification product does not include peptides that result from either incomplete transcription or translation, because such peptides do not contain the C-terminal tag. It will be understood by one of ordinary skill in the art that any combination of different N-terminal and C-terminal tags will be useful for this two step purification procedure.

The processes described above are amenable to multiplexing at numerous levels. Multiplexing can be done at the MALDI-TOF instrument stage where multiple purified proteins are combined and placed together on the same spot, or at the purification level, where multiple synthesis reactions are pooled before adding beads and purifying. Multiplexing can also be done at the protein synthesis stage by pooling multiple PCR products in one synthesis reaction, or even at the PCR amplification step by using multiple primer pairs. Once a step is multiplexed, all downstream steps will be multiplexed as well resulting in increased throughput and reduced cost.

In one embodiment, the in-vitro synthesized proteins can be degraded by either endopeptidases or exopeptidases that are endogenous to the lysate or that are added exogenously. In many cases the analysis of peptide fragments generated by proteolytic degradation provides additional information that cannot be obtained by looking only at the intact protein. For example, proteins can be sequenced by determining the mass of fragments resulting from partial degradation by carboxypeptidase and other proteases. For example, identification of large peptides or proteins can be facilitated by trypsin digestion. MALDI-TOF analysis of trypsin digests of large proteins improves sensitivity and resolution due to the relative ease of ionizing small peptides in addition to providing partial sequence information. Although the examples presented below rely only on MALDI-TOF analysis, other mass spectrometric methods of analysis of the purified in-vitro synthesized proteins are possible.

The in-vitro synthesized proteins must be ionized before they can be detected by MALDI. Certain residues within the peptide, such as arginine, are particularly good at facilitating ionization, and the peptide tag could include a number or such residues in order to aid the ionization process.

The in-vitro synthesis reaction requires the addition of exogenously added amino acids. Therefore one could add isotopic variants of leucine or isoleucine in order to discriminate between these two amino acids by mass.

In one embodiment of the invention, one or more amino acid isotopes are included in the in-vitro translation reaction. The resulting in-vitro synthesized test peptides contain isotopic variants not found in the initial lysate and are easily identified when analyzed by mass spectrometry. Accordingly, mass spectrometry can be used to assay the synthesized product without purifying it. In a preferred embodiment, amino acid isotopes are included in the translation reaction, and the synthetic peptide contains an amino or carboxy terminal tag with specific amino acids that produce a characteristic pattern in mass spectrometry. For example, when 50% of the cysteine in the lysate is sulfur 35 labeled (the other 50% will have the more common sulfur 32 isotope) and a cysteine residue is included in the tag, a test peptide possessing only one cysteine will appear as a doublet separated by 3 mass units in the spectrum. Such a doublet will be characteristic of a newly synthesized peptide and can be discriminated from other molecules in the lysate.

Many mutations and polymorphisms result in alterations in restriction endonuclease cleavage sites. Such alterations can be easily detected by treating a PCR product with the appropriate endonuclease and analyzing the digested fragments. The digested PCR products could be used to make in-vitro synthesized proteins that could be detected by MALDI-TOF. Alterations in a restriction site would affect the mass of the protein product in a predictable manner.

In one embodiment of the invention, a coding region is assayed using a series of 5' and 3' primer pairs. Each pair amplifies an adjacent or overlapping fragment of the coding region. In a preferred embodiment, a primer pair amplifies between 30 and 300 coding nucleotides. In more preferred embodiment, a primer pair amplifies 60 to 120 coding nucleotides, and more preferably about 90 coding nucleotides. In an alternative embodiment, a primer pair amplifies less than 30 coding nucleotides. In a further embodiment, a primer pair amplifies more than 300 coding nucleotides. Accordingly, the invention provides for a kit containing a series of primer pairs to assay the entire coding region of a gene of interest. In one embodiment of the invention, each primer pair is used in a separate assay. In a preferred embodiment, the products of several primer pairs are assayed in a single multiplex reaction. Preferably, each primer pair is used in a separate PCR reaction, and the different PCR products are combined (multiplexed) for the transcription and translation reactions. The resulting peptide products are separated by mass spectrometry and evaluated using predetermined standards. In a most preferred embodiment, a protease inhibitor is added to a multiplexed translation reaction to minimize the presence of partial degradation products. Such degradation products would complicate the mass spectrometry analysis of multiplexed translation products.

EXAMPLE 1

Materials and Methods

Two overlapping and complimentary oligonucleotides were designed to test the concept of analyzing in-vitro synthesized peptides by mass spectrometry. The oligonucleotide sequences were 5'-ATACGACTCACTATAGGGAG-ACCACCATGGACTACAAGGACGACGATGACAAG-GCTTGTGAATTTTCTGAGACG-3' (SEQ ID No. 9) for the 5' primer and 5'-CCCAAATCAGGCGGCGGCCCAA-CCCGTCTCAGAAAATTCACAAGC-3' (SEQ ID No. 10) for the 3' primer. When extended by cycling 10 times with Taq polymerase in a standard PCR reaction, these 2 oligonucleotides generate a double stranded DNA PCR product possessing a T7 polymerase binding site, a Kozak consensus sequence with an initiator methionine codon, 8 in frame codons encoding the Flag peptide DYKDDDDK (SEQ ID No. 2), 13 codons in frame encoding the test peptide ACEFESTGWAAA (SEQ ID No. 11), the stop codon TGA, and the additional sequence TTTGGG. The entire peptide (which will be referred to as peptide 1) encoded by this template has 21 residues and a predicted mass of 2369 Daltons. 19 ul of the raw PCR product were added to 31 ul of TNT coupled wheat germ extract system capable of performing coupled transcription/translation (Promega Corporation, Madison Wis., catalog number L4140). The reaction was allowed to proceed for 1 hour at 30 degrees, and then 2 ul of the anti-Flag M2 affinity gel(Sigma Chemicals, Saint Louis, Mo., catalog number A1205) were added to the lysate and shaken at room temperature for 20 minutes. The beads were washed by placing the beads on a filter, applying a vacuum, and washing with 2 ml of 25 mM ammonium bicarbonate pH 8.0.

Figure 3A:
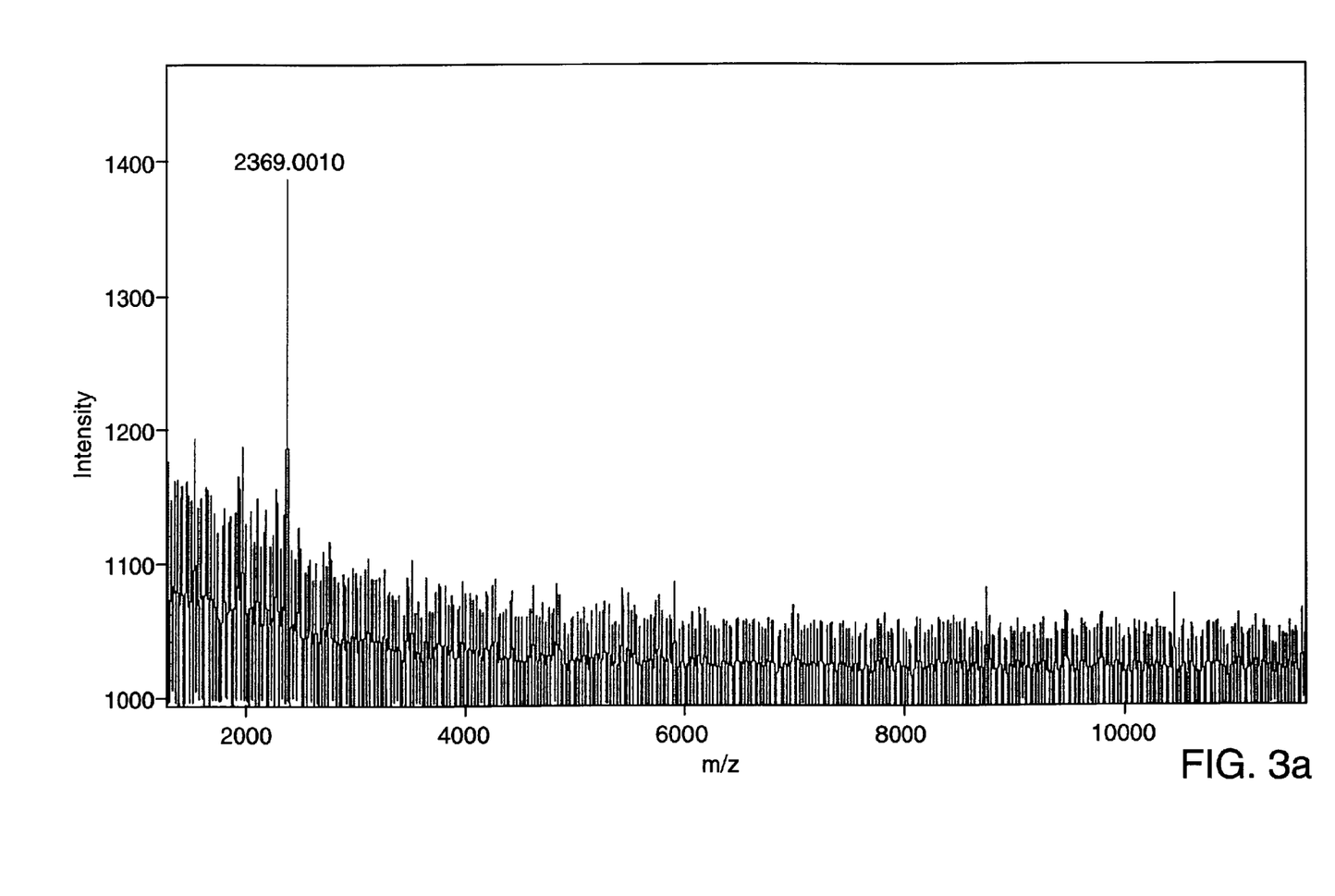
FIGS. 3a and 3b depict two views of the same MALDI-TOF spectrum of test peptide 1 having the sequence MDYKDDDDKACEFSETGWAAA (SEQ ID No. 1). The peptide was made by in-vitro translation, purified with anti-Flag beads which recognize the sequence DYKDDDDK (SEQ ID No. 2), and analyzed by MALDI-TOF.
Figure 3B:
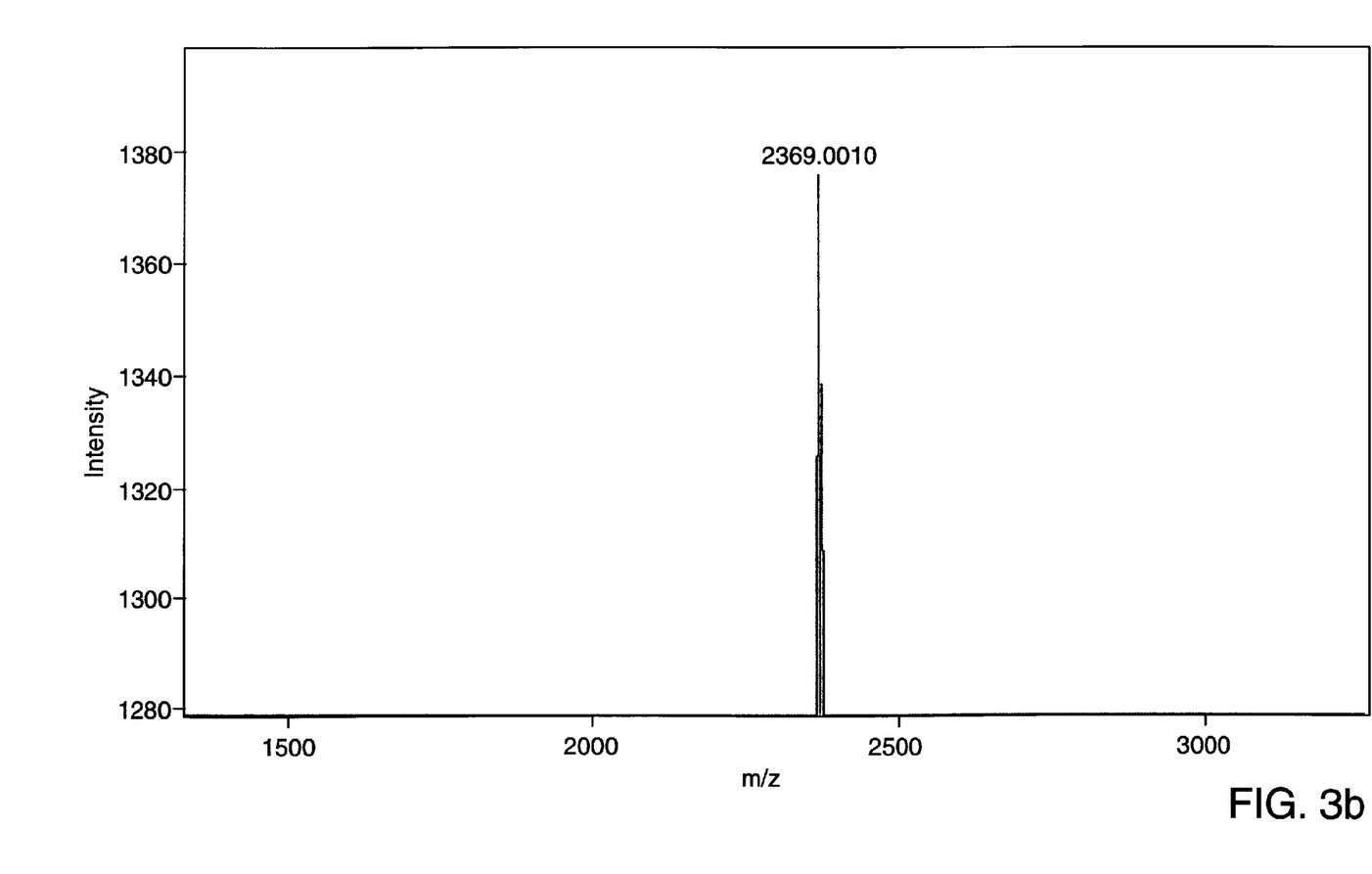

The washed beads were resuspended in 2 ul of 10 mg/ml alpha-cyano-4-hydroxycinnamic acid (Sigma, catalog number C-2020) matrix dissolved in 50% acetonitrile, 0.1% TFA in water. 1 ul of the matrix/peptide mixture was spotted onto a MALDI sample plate and analyzed by DE-MALDI-TOF using a Voyager Pro instrument (PerSeptive Biosystems, Framingham, Mass.). FIG. 3a shows the spectrum over the m/z range of 1,300–12,000. One dominant peak of 2369 corresponding to a singly charged peptide of the expected mass is present. FIG. 3b presents a close-up of the peak.

EXAMPLE 2

Figure 4:
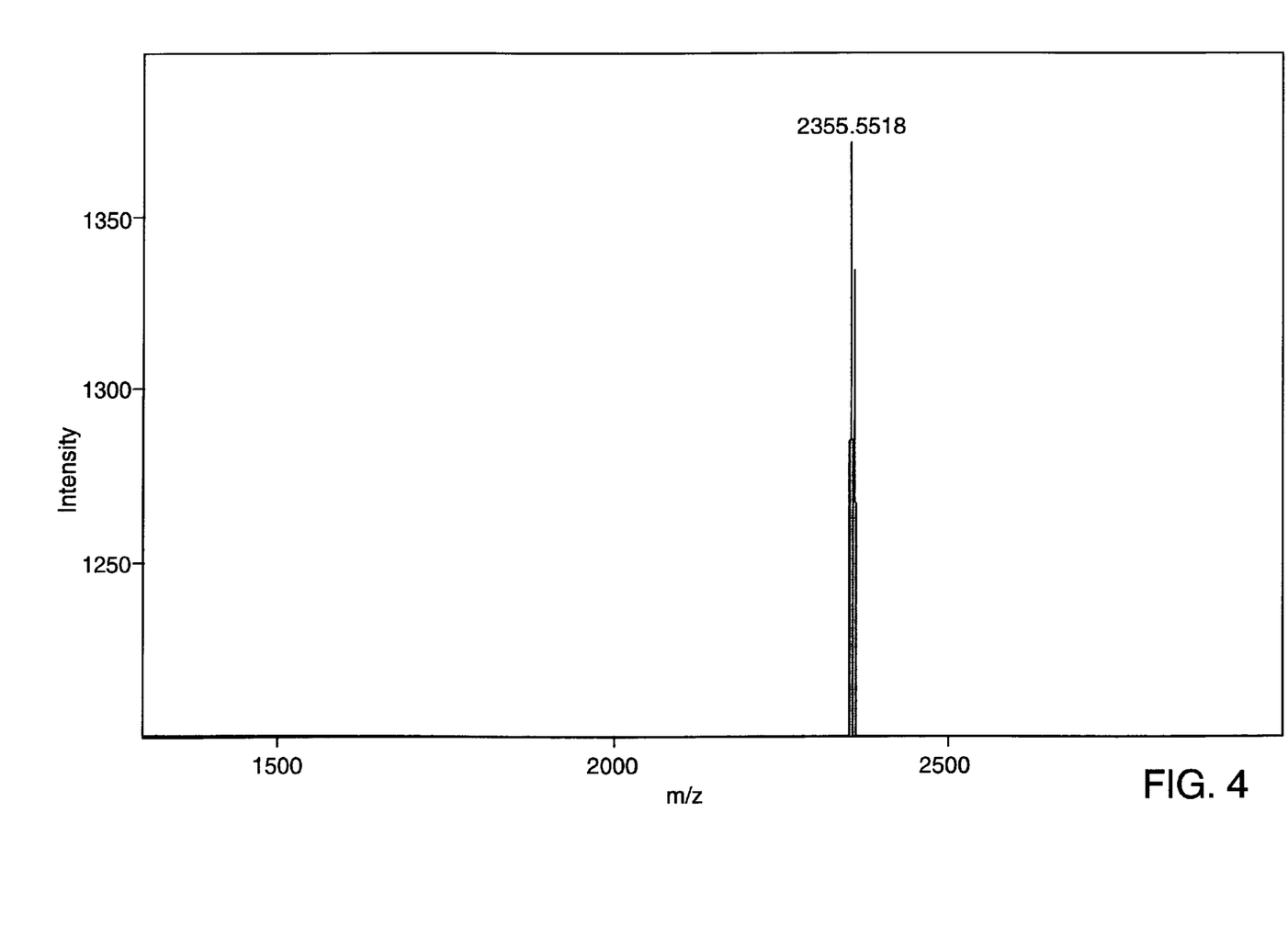
FIG. 4 depicts a MALDI-TOF spectrum of test peptide 2 having the sequence MDYKDDDDKACEFSETGWAAG (SEQ ID No. 3), which differs from peptide 1 only at the carboxy terminal residue.

A second test peptide was synthesized using the same 5' oligonucleotide from Example 1, and a different 3' oligonucleotide having the following sequence: 5'-CCCA-AATCAACCGGCGGCCCAACCCGTCTCAGAAAATT-CACAAGC-3' (SEQ ID No. 12). The peptide encoded by the PCR product generated with this oligo pair is identical to that made in example 1 except that the carboxy terminal alanine has been changed to a glycine. The predicted mass of this peptide, referred to as peptide 2, is 2,355 Daltons. FIG. 4 shows the spectrum of peptide 2. A dominant peak at 2,355 corresponds to a singly charged peptide of the expected mass.

EXAMPLE 3

Figure 5A:
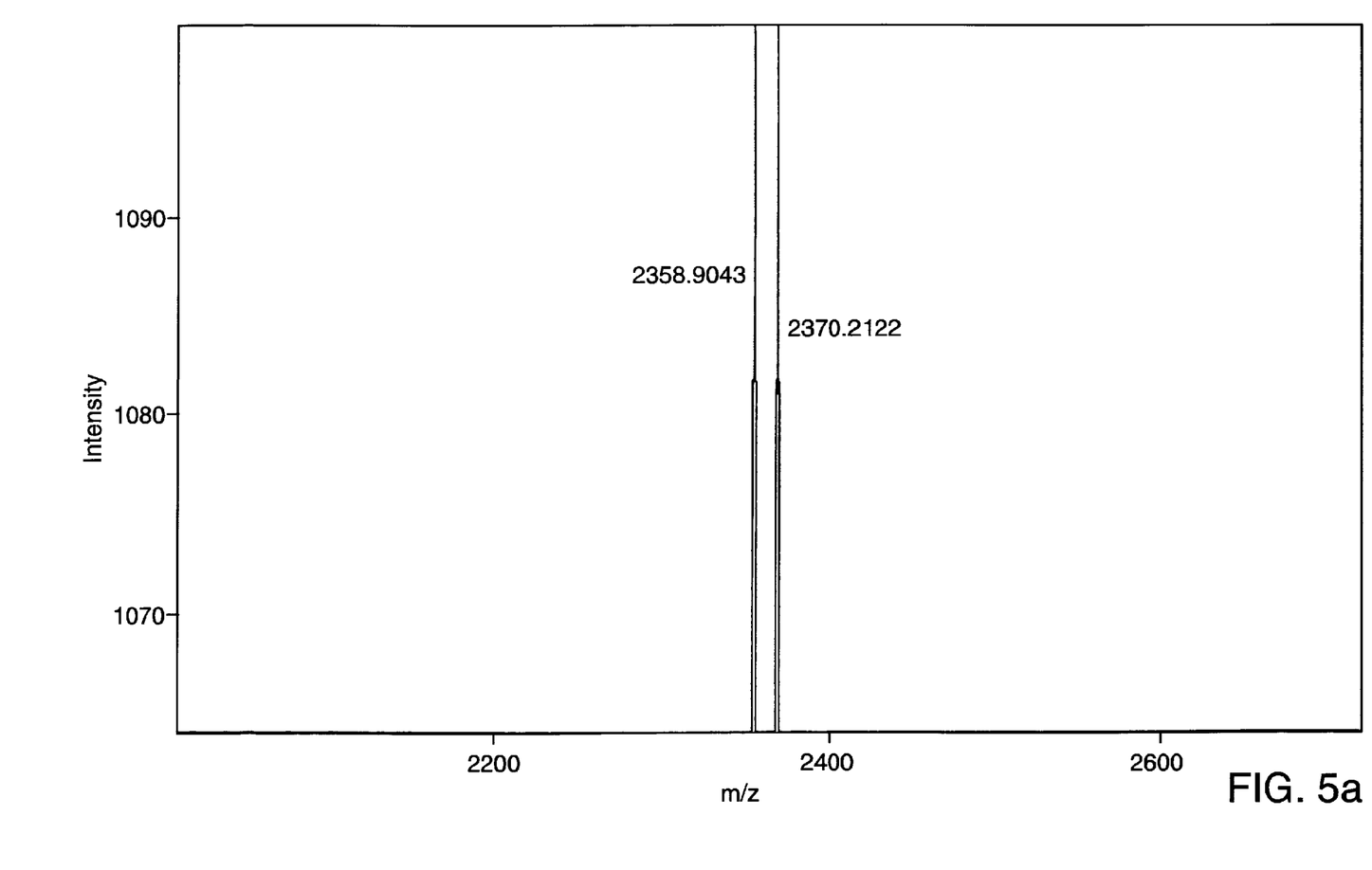
FIGS. 5a and 5b are two views of a MALDI-TOF spectrum obtained from in-vitro synthesized proteins made from a mixture of the DNA templates used to make peptides 1 and 2.
Figure 5B:
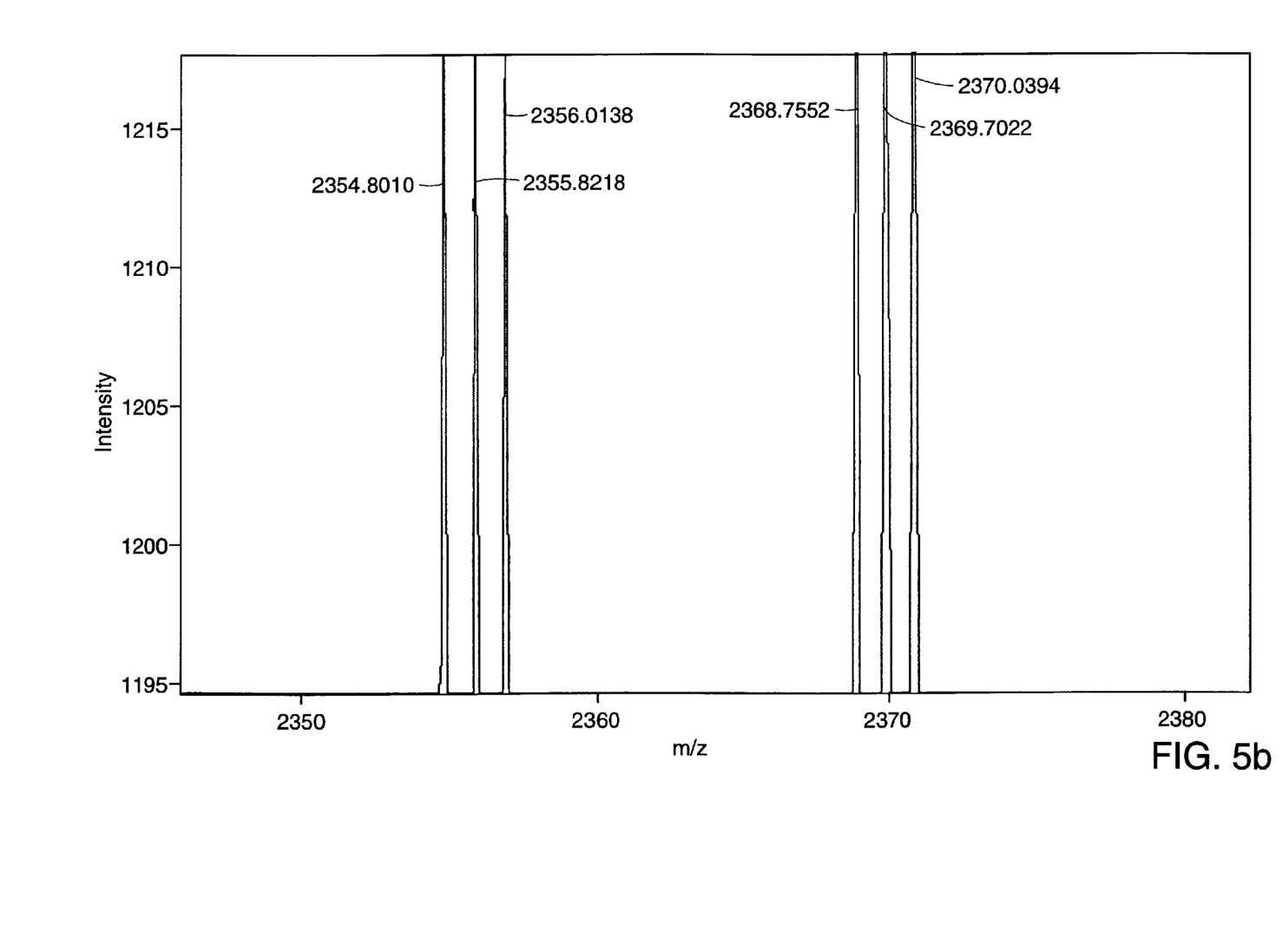

Mutation detection will often entail detection of 2 signals present in a heterozygote. 8.5 ul of PCR products encoding peptides 1 and 2 were mixed together and added to 31 ul of wheat germ lysate to mimic what would happen if DNA from a heterozygote were used as template for a PCR amplification. The resulting spectrum of the in-vitro synthesized peptides is shown in FIG. 5a. Two peaks corresponding to peptides 1 and 2 are clearly seen. FIG. 5b presents a close-up of the spectrum with mono-isotopic resolution being apparent. Each of the 3 peaks for peptides 1 and 2 are separated by 1 m/z unit, and the corresponding peaks (i.e., the smallest peak in peptide 1 and the smallest peak in peptide 2) are separated by 14 m/z units, exactly what is predicted for a glycine-alanine substitution.

EXAMPLE 4

Figure 6:
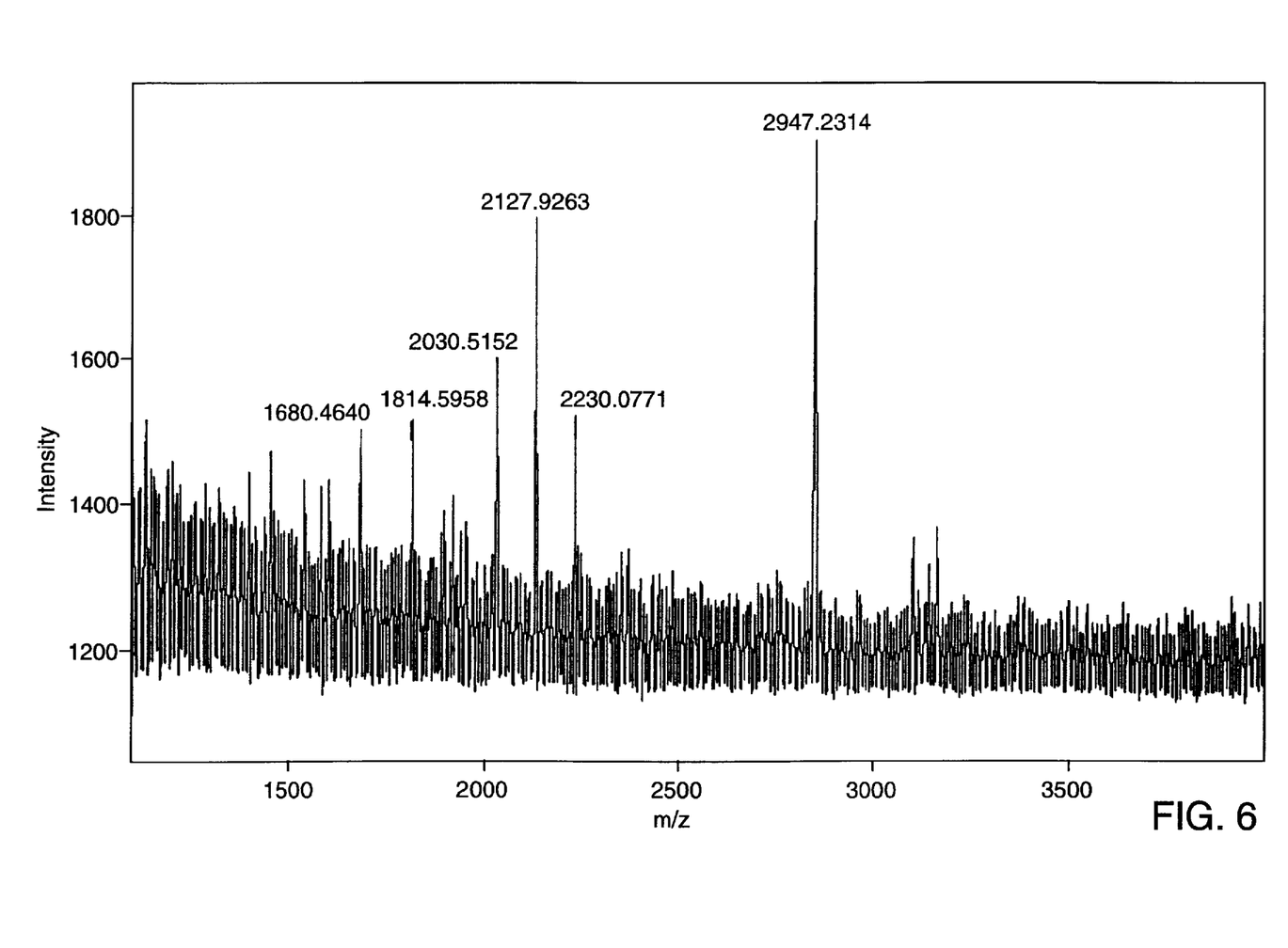
FIG. 6 is a MALDI-TOF spectrum obtained from in-vitro synthesized proteins made from a PCR product amplified from genomic DNA template. The 24 residue peptide MDYKDDDDKACEFSETDVTNTEHH (SEQ ID No. 4) consists of the Flag sequence attached to the first 15 codons of exon 11 of the BRCA1 gene.

In a clinical or research setting, genetic analysis is done on PCR products amplified using DNA as template rather than overlapping oligonucleotides as were used in examples 1–3. In order to demonstrate that MALDI analysis of in-vitro synthesized proteins can be done using human genomic DNA as starting material, The first 15 codons of exon 11 of the human BRCA1 gene were amplified from 100 ng of genomic DNA in a standard PCR amplification. 35 cycles of amplification were performed using the 5' primer given in example 1 and a 3' primer with the following sequence: 5'-ATTAACCCTCACTAAAGGGATCAATGATGTTCAG-TATTTGTTAC-3' (SEQ ID No. 13). The resulting PCR product encodes a peptide 24 residues in length consisting of the N terminal methionine, the 8 residue flag sequence and the 15 residues of BRCA1 with a predicted mass of 2847 Daltons. Again, 19 ul of raw PCR product were added to 31 ul of wheat germ lysate and the test protein was purified and analyzed by MALDI. FIG. 6 shows the spectrum of this peptide and a major peak at 2847 corresponds to the full length singly charged peptide. Additional smaller peaks are also apparent at 2127, 1810, and 1681 which correspond to masses resulting from either degradation products or incomplete extensions creating peptides that lack 5, 8, and 9 residues at the carboxy terminus, respectively.

The process described above involves a series of steps that can be performed in most well equipped biomedical laboratories. In order to facilitate the rapid acceptance and usage of this process, many of the essential components may be assembled and provided in a kit. The following consumable reagents (or a subset thereof) may be provided in such a kit: (1) reagents for PCR amplification such as Taq polymerase, nucleotides, and buffers; (2) 5' primers and 3' primers of the invention, such as polynucleotides for PCR amplification of test sequences which contain an RNA polymerase promoter, an mRNA translation initiator site, e.g., a Kozak consensus sequence with an AUG initiator, and a peptide tag, e.g., FLAG sequences; (3) cell lysate for coupled in-vitro transcription/translation including cell extract, amino acids, RNA polymerase, ribonucleotides, buffer, and Riase inhibitor; (4) an affinity ligand for the peptide tag coupled to a solid support; (5) vacuum filters, centrifugal, or magnetic purification devices for washing the solid support. A kit may contain one primer or set of primers for a particular gene mutation. However, a kit may include multiple primers and/or sets of primers for detecting multiple gene mutations or for overlapping sequences for one particular gene mutation.

It is thus apparent that the use of tagged in-vitro synthesized proteins provide advantages over untagged proteins in terms of how they can be analyzed and the quality of data obtained. The tag can be used to purify the protein away from other components of the lysate and to concentrate the protein on the solid support on which the ligand for the tag is attached. To date, the exquisite accuracy, sensitivity, and throughput of certain protein analytical techniques, such as mass spectrometry, have yet to be applied to mutation detection. The ability to easily purify in-vitro synthesized proteins in accordance with the method of this invention will facilitate the use of these techniques in helping to identify mutations and polymorphisms in genes.

Modifications to the methods and kit described herein are possible without departing from the scope of the present invention. Such modifications and equivalents are intended to be covered by the scope of the following claims.

What is claimed is:

1. A method for detecting a protein altering mutation in a test sequence of a gene comprising:
   (a) amplifying the test sequence of the gene using a 5' primer, the 5' primer comprising, from its 5' to 3' direction:
      (i) an RNA polymerase promoter;
      (ii) a mRNA translation initiation site;
      (iii) a polynucleotide sequence encoding a peptide tag; and
      (iv) a polynucleotide sequence that hybridizes to a sequence on the non-coding strand adjacent to the 5' end of the test sequence;
   (b) transcribing in-vitro the product of step (a);
   (c) translating in-vitro the product of step (b);
   (d) purifying the product of step (c) by affinity purification using the peptide tag; and
   (e) analyzing the purified product of step (d) by mass spectrometry to determine whether a protein altering mutation is present in the test sequence.

2. The method of claim 1 wherein step (d) comprises affinity chromatography.

3. The method of claim 1 wherein amplifying the test portion of the gene further comprises using a 3' primer, the 3' primer comprising a polynucleotide sequence that hybridizes to a sequence on the coding strand adjacent to the 3' end of the test sequence.

4. The method of claim 1 wherein the mass spectrometry is matrix assisted laser desorption ionization time-of-flight (MALDI-TOF) mass spectrometry.

5. The method of claim 1 wherein step (e) comprises comparing the mass of the product of step (d) to the mass of a product of step (d) wherein the test sequence of a gene is the wild type sequence.

6. The method of claim 1 wherein the peptide tag comprises an amino acid that produces a characteristic pattern in mass spectrometry.

7. The method of claim 1 wherein the gene is BRCA1 or BRCA2.

8. A method for detecting a protein altering mutation in a test sequence of a gene comprising:
   (a) amplifying the test sequence of the gene using a 5' primer and a 3' primer, the 5' primer comprising, from its 5' to 3' direction:
      (i) an RNA polymerase promoter;
      (ii) an mRNA translation initiation site; and
      (iii) a polynucleotide sequence that hybridizes to a sequence on the non-coding strand adjacent to the 5' end of the test sequence; and
   the 3' primer comprising, from its 5' to 3' direction:
      (i) a non-coding sequence that is complimentary to a sequence encoding a peptide tag; and
      (ii) a polynucleotide sequence that hybridizes to a sequence on the coding strand adjacent to the 3' end of the test sequence;
   (b) transcribing in-vitro the product of step (a);
   (c) translating in-vitro the product of step (b);
   (d) purifying the product of step (c) by affinity purification using the peptide tag; and
   (e) analyzing the purified product of step (d) by mass spectrometry to determine whether a protein altering mutation is present in the test sequence.

9. The method of claim 1 further comprising the step of:
   (f) determining nucleotide information of the test sequence of the gene.

10. The method of claim 1 wherein phenylmethylsulfonylfluoride (PMSF) is included in the translation reaction of step (c).

\* \* \* \* \*

SEQUENCE LISTING

```
<160> NUMBER OF SEQ ID NOS: 13

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence:  Test
      peptide 1

<400> SEQUENCE: 1

Met Asp Tyr Lys Asp Asp Asp Asp Lys Ala Cys Glu Phe Ser Glu Thr
 1               5                  10                  15

Gly Trp Ala Ala Ala
            20

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:  Flag
      peptide

<400> SEQUENCE: 2

Asp Tyr Lys Asp Asp Asp Asp Lys
 1               5
```

```
<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence:  Test
      peptide 2

<400> SEQUENCE: 3

Met Asp Tyr Lys Asp Asp Asp Lys Ala Cys Glu Phe Ser Glu Thr
 1               5                  10                  15

Gly Trp Ala Ala Gly
            20

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence:  In vitro
      synthesized peptide

<400> SEQUENCE: 4

Met Asp Tyr Lys Asp Asp Asp Lys Ala Cys Glu Phe Ser Glu Thr
 1               5                  10                  15

Asp Val Thr Asn Thr Glu His His
            20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:  T7
      polymerase recognition sequence

<400> SEQUENCE: 5
taatacgact cactataggg                                                 20

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence:  Kozak
      consensus sequence

<400> SEQUENCE: 6
agaccaccat g                                                          11

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide encoding the FLAG peptide

<400> SEQUENCE: 7
gactacaagg acgacgatga caag                                            24

<210> SEQ ID NO 8
<211> LENGTH: 20
<212> TYPE: DNA
```

```
<213> ORGANISM: Artificial Sequence
<220> FEATURE:
<223> OTHER INFORMATION: Description of Artificial Sequence:
      Oligonucleotide complementary to the 5' non-coding
      strand of exon 11 of the BRCA1 gene

<400> SEQUENCE: 8
gcttgtgaat tttctgagac                                                   20

<210> SEQ ID NO 9
<211> LENGTH: 74
<212> TYPE: DNA
<213> ORGANISM: Artificial Sequence
<220> FEATURE:
<223> OTHER INFORMATION: Description of Artificial Sequence:  5' primer
      oligonucleotide

<400> SEQUENCE: 9
atacgactca ctatagggag accaccatgg actacaagga cgacgatgac aaggcttgtg       60
aattttctga gacg                                                         74

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence:  3' primer
      oligonucleotide

<400> SEQUENCE: 10
cccaaatcag gcggcggccc aacccgtctc agaaaattca caagc                       45

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence:  Test
      peptide

<400> SEQUENCE: 11

Ala Cys Glu Phe Glu Ser Thr Gly Trp Ala Ala Ala
 1               5                  10

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence:  3' primer
      oligonucleotide

<400> SEQUENCE: 12
cccaaatcaa ccggcggccc aacccgtctc agaaaattca caagc                       45

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence:  3' primer
      oligonucleotide

<400> SEQUENCE: 13
attaaccctc actaaaggga tcaatgatgt tcagtatttg ttac                        44
```